US009416386B2

(12) United States Patent
Saito et al.

(10) Patent No.: US 9,416,386 B2
(45) Date of Patent: Aug. 16, 2016

(54) CDNA SYNTHESIS METHOD

(71) Applicant: Seiko Epson Corporation, Tokyo (JP)

(72) Inventors: Yuji Saito, Shiojiri (JP); Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/203,994

(22) Filed: Mar. 11, 2014

(65) Prior Publication Data

US 2014/0273100 A1 Sep. 18, 2014

(30) Foreign Application Priority Data

Mar. 13, 2013 (JP) ................. 2013-050659

(51) Int. Cl.
*C12Q 1/68* (2006.01)
*C12P 19/34* (2006.01)
*C12N 15/10* (2006.01)
*C07H 21/02* (2006.01)

(52) U.S. Cl.
CPC ............. *C12P 19/34* (2013.01); *C12N 15/1096* (2013.01)

(58) Field of Classification Search
CPC ................... C12Q 2565/537; C12Q 2525/173; C12Q 1/6834; C12N 15/1096
See application file for complete search history.

(56) References Cited

U.S. PATENT DOCUMENTS

| 5,990,302 A * | 11/1999 | Kuroita et al. ............... 536/25.4 |
| 2005/0153292 A1 * | 7/2005 | Stordeur .............. C12Q 1/6806 435/6.16 |
| 2005/0232934 A1 * | 10/2005 | Chen .................... C12N 9/1276 424/188.1 |
| 2013/0303382 A1 * | 11/2013 | Pollner ................ C12Q 1/6834 506/2 |

FOREIGN PATENT DOCUMENTS

| EP | 1930422 A1 | 6/2008 |
| EP | 1964920 A1 | 9/2008 |
| JP | 11-146783 | 6/1999 |
| WO | WO-93-15228 A1 | 8/1993 |
| WO | WO-98-51699 A1 | 11/1998 |
| WO | WO-99-32654 A1 | 7/1999 |
| WO | WO-01-51601 A2 | 7/2001 |

OTHER PUBLICATIONS

Rogers, C.D.G. et al., Biotechnol. Appl. Biochem., vol. 31, pp. 219-224 (2000).*
Plante, D. et al., Letters in Appl. Microbiol., vol. 52, pp. 239-244 (2011).*
Stratagene Catalog, p. 39 (1988).*
Auld, D.S. et al., PNAS USA, vol. 71, pp. 2091-2095 (1974).*
Boom, R. et al., "Rapid and simple method for purification of nucleic acids", Journal of Clinical Microbiology, vol. 28, No. 3, pp. 495-503, 1990.
Extended European Search Report for Application No. EP 14 15 9126 dated Sep. 17, 2014 (11 pages).
Fellmann F. et al., "Simplified Protocol of Solid-Phase cDNA Libraries for Multiple PCR Amplification", Biotechniques, Informa Healthercare, U.S., vol. 21, No. 5, Nov. 1, 1996, pp. 766-770.
Lambert, K. et al., "cDNA Library Construction From Small Amounts of RNA Using Paramagnetic Beads and PCR", Nucleic Acids Research, Oxford University Press, vol. 21, No. 3, Jan. 1, 1993, pp. 775-776.
Roeder, T., "Solid -Phase cDNA Library Construction, A Versatile Approach", Nucleic Acids Research, Oxford University Press, vol. 26, No. 14, Jun. 1, 1998, pp. 3451-3452.
Meszaros M. et al., "Subtractive Hybridization Strategy Using Paramagnetic Oligo(dT) Beads and PCR", Biotechniques, Informa Healterhcare, U.S., vol. 20, No. 3, Jan. 1, 1996 pp. 413-419.
Sasaki, Y. et al., "Construction of a Normalized cDNA Library by Introduction of a Semi-Solid mRNA-cDNA Hybridization System", Nucleic Acids Research, Oxford University Press, vol. 22, No. 6, Feb. 1, 1994, pp. 987-992.
Raineri, I., et al., "Improved Efficiency for Single-Sided PCR by Creating a Reusable Pool of First-Strand cDNA Coupled to a Solid Phase", Nucleic Acids Research, Oxford University Press, vol. 19, No. 14, Jul. 25, 1991, p. 4010.
Hamaguchi, Y., et al., "Direct Reverse Transcription-PCR on Oligo(dT)-Immobilized Polypropylene Microplates After Capturing Total mRNA From Crude Cell Lysates", Clinical Chemistry, American Association for Clinical Chemistry, Washington, DC, vol. 44, No. 11, Jan. 1, 1998, pp. 2256-2263.
Augenstein, S., "Superparamagnetic Beads: Applications of Solid-Phase RT-PCR", American Laboratory, International Scientific Communications, Inc., U.S., vol. 12, No. 6, May 1, 1994, pp. 12-14.

* cited by examiner

*Primary Examiner* — Teresa E Strzelecka
(74) *Attorney, Agent, or Firm* — Harness, Dickey & Pierce, P.L.C.

(57) ABSTRACT

A cDNA synthesis method includes: mixing a lysis solution containing a chaotropic substance and a nucleic acid-binding solid-phase carrier in a sample containing a ribonucleic acid (RNA), thereby adsorbing the RNA on the carrier; reverse-transcribing the RNA adsorbed on the carrier while keeping the RNA adsorbed on the carrier in a reverse transcription reaction mixture, thereby synthesizing cDNA; and eluting the synthesized cDNA with an eluent.

7 Claims, 1 Drawing Sheet

SEQUENCE LISTING

<160> NUMBER OF SEQ ID NOS: 3

<210> SEQ ID NO 1
<211> LENGTH: 22
<212> TYPE: DNA
<213> ORGANISM: Influenza A virus

<400> SEQUENCE: 1
gaccaatcct gtcacctctg ac                                              22

<210> SEQ ID NO 2
<211> LENGTH: 24
<212> TYPE: DNA

```
<213> ORGANISM: Influenza A virus

<400> SEQUENCE: 2
agggcatttt ggacaaagcg tcta                                            24

<210> SEQ ID NO 3
<211> LENGTH: 24
<212> TYPE: DNA
<213> ORGANISM: Influenza A virus

<400> SEQUENCE: 3
tgcagtcctc gctcactggg cacg                                            24
```

CDNA SYNTHESIS METHOD

BACKGROUND

1. Technical Field

The present invention relates to a cDNA synthesis method.

2. Related Art

There has been reported by Boom et al. a method for more easily extracting nucleic acids from a biomaterial using a nucleic acid-binding solid-phase carrier such as silica particles and a chaotropic agent (see J. Clin. Microbiol., vol. 28, No. 3, pp. 495-503 (1990)). A method for extracting nucleic acids using a nucleic acid-binding solid-phase carrier such as silica and a chaotropic agent by adsorbing nucleic acids on the carrier including this method of Boom et al. mainly includes the following three steps: (1) a step of adsorbing nucleic acids on a nucleic acid-binding solid-phase carrier in the presence of a chaotropic agent (adsorption step); (2) a step of washing the carrier having the nucleic acids adsorbed thereon with a washing solution for removing nonspecifically bound contaminants and the chaotropic agent (washing step); and a step of eluting the nucleic acids from the carrier using water or a low salt concentration buffer (elution step). Here, as the washing solution used in the step (2), water or a low salt concentration buffer containing a water-soluble organic solvent, particularly ethanol in an amount of about 50 to 80% has been used for dissolving the chaotropic agent and also preventing the elution of the nucleic acids from the carrier.

However, when this water-soluble organic solvent remains in the step (3), an enzymatic reaction is inhibited when the extracted liquid is treated with an enzyme. Therefore, generally, after washing with an aqueous solution containing ethanol, a procedure is performed such that washing with 100% ethanol or a solvent having a higher volatility such as acetone is performed as needed, followed by drying so as to completely remove the organic solvent from the system. However, this procedure is known to have a problem that it takes a lot of time for this drying, and also ethanol may remain if the drying time is not sufficient, and in extreme cases, the nucleic acids are dried out and solidified, and therefore, it becomes difficult to elute the nucleic acids, resulting in a decrease in the yield of nucleic acids or a deterioration in reproducibility. Accordingly, the use of an organic solvent as described above has a problem that it is difficult to check the degree of dryness, and also an organic solvent such as ethanol or acetone is flammable and volatile, and therefore, particularly in the case of assuming that the operation is automated, it is also considered that there is a risk of fire or the like.

Accordingly, a method in which after nucleic acids are adsorbed on the carrier, the carrier is washed with water or a low salt concentration buffer which contains no organic solvents such as ethanol in the washing step (2), and the nucleic acids are eluted with water or a low salt concentration buffer at 50 to 70° C. in the elution step (3), whereby ribonucleic acids (RNA) are extracted has been developed (see JP-A-11-146783).

SUMMARY

An advantage of some aspects of the invention is to provide a cDNA synthesis method which enables the synthesized cDNA to be efficiently used.

Heretofore, in the Boom method, nucleic acids are adsorbed on a carrier, and the carrier is washed with water or a low salt concentration buffer which contains substantially no organic solvents such as ethanol in the washing step (2), and thereafter the nucleic acids are eluted with water or a low salt concentration aqueous solution at 50 to 70° C. in the elution step (3), whereby a ribonucleic acid (RNA) is isolated (JP-A-11-146783). However, the present inventors found out that in the case of using RNA isolated by the Boom method in RT-PCR, by reverse-transcribing the RNA adsorbed on the carrier without releasing the RNA from the carrier, the synthesized cDNA can be directly eluted in the PCR reaction mixture so that the following PCR reaction can be efficiently performed, and thus completed the invention.

A cDNA synthesis method according to an aspect of the invention includes: mixing a lysis solution containing a chaotropic substance and a nucleic acid-binding solid-phase carrier in a sample containing a ribonucleic acid (RNA), thereby adsorbing the RNA on the carrier; reverse-transcribing the RNA adsorbed on the carrier while keeping the RNA adsorbed on the carrier in a reverse transcription reaction mixture, thereby synthesizing cDNA; and eluting the synthesized cDNA with an eluent. The method may further include washing the carrier having the RNA adsorbed thereon with a washing solution which does not contain an organic solvent before or after the reverse transcription. The reverse transcription reaction mixture may contain a reverse transcriptase, dNTP, and a primer for reverse transcription. The eluent may contain a DNA polymerase, dNTP, and primers for DNA amplification. The reverse transcription reaction mixture and/or the eluent may contain BSA. Further, in the reverse transcription, the RNA is preferably reverse-transcribed at a temperature lower than 50° C. The carrier is preferably a magnetic particle.

A cDNA synthesis kit according to another aspect of the invention includes: a neutral lysis solution containing 4 to 7 M of a guanidine salt, 0 to 5% of a nonionic surfactant, and 0 to 0.2 M of a reducing agent; a nucleic acid-binding solid-phase carrier; a first washing solution containing 4 to 7 M of a guanidine salt and 0 to 5% of a nonionic surfactant; a second washing solution composed of water or a low salt concentration aqueous solution; a reverse transcription reaction mixture containing a reverse transcriptase, dNTP, and a primer for reverse transcription; and a DNA amplification mixture containing a DNA polymerase, dNTP, and primers for DNA amplification.

According to the aspects of the invention, a cDNA synthesis method which enables the synthesized cDNA to be efficiently used can be provided.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
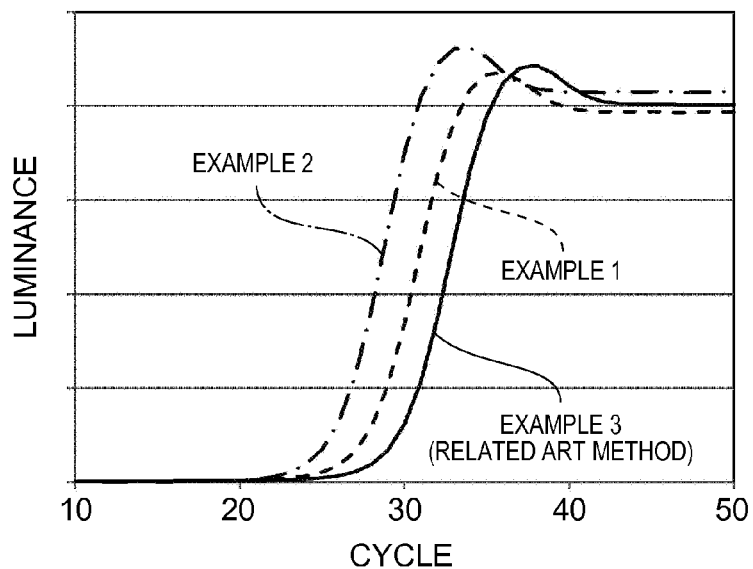
FIG. 1 is a graph showing the results obtained by performing a PCR reaction using cDNA synthesized by performing a reverse transcription reaction on a carrier in an example of the invention.

Unless otherwise specifically stated in embodiments and Examples, methods described in standard protocols such as M. R. Green & J. Sambrook (Ed.), Molecular cloning, a laboratory manual (4th edition), Cold Spring Harbor Press, Cold Spring Harbor, N.Y. (2012); F. M. Ausubel, R. Brent, R.

E. Kingston, D. D. Moore, J. G. Seidman, J. A. Smith, K. Struhl (Ed.), and Current Protocols in Molecular Biology, John Wiley & Sons Ltd., or modified or altered methods thereof are used. Further, when commercially available reagent kits, or measurement devices are used, unless otherwise specifically stated, protocols attached thereto are used.

The objects, features, advantages, and ideas of the invention are apparent to those skilled in the art from the description of this specification, and those skilled in the art can easily reproduce the invention from the description of this specification. The modes, specific Examples, etc. of the invention described below represent preferred embodiments of the invention, which are given for the purpose of illustration or description, and the invention is not limited thereto. It is obvious to those skilled in the art that various modifications and changes may be made based on the description of the specification without departing from the spirit and scope of the invention disclosed herein.

Reagent for cDNA Synthesis

The cDNA synthesis method according to the invention includes: an adsorption step in which a lysis solution containing a chaotropic substance and a nucleic acid-binding solid-phase carrier are mixed in a sample containing RNA, whereby the RNA is adsorbed on the carrier; a reverse transcription step in which the RNA adsorbed on the carrier is reverse-transcribed while keeping the RNA adsorbed on the carrier in a reverse transcription reaction mixture, whereby cDNA is synthesized; and an elution step in which the synthesized cDNA is eluted with an eluent. The method may further include a washing step in which the carrier having the RNA adsorbed thereon is washed with a washing solution before the reverse transcription step.

The sample from which RNA is extracted is not particularly limited as long as the sample contains RNA, and may be a biological sample such as cells or cell clusters (such as tissues), viruses, synthetic RNA, a sample in which impurities or contaminants are mixed with once isolated RNA, or the like.

The chaotropic substance is not particularly limited as long as it generates a chaotropic ion (a monovalent anion having a large ionic radius) in an aqueous solution, has an activity to increase the water solubility of a hydrophobic molecule, and contributes to the adsorption of RNA on the solid-phase carrier. Specific examples thereof include guanidine thiocyanate, guanidine hydrochloride, sodium iodide, potassium iodide, and sodium perchlorate. Among these, guanidine thiocyanate or guanidine hydrochloride having a high protein denaturation activity is preferred. The concentration of such a chaotropic substance is not particularly limited and varies depending on the respective substances, and for example, when guanidine thiocyanate is used, the concentration thereof is preferably in the range of 3 to 5.5 M, and when guanidine hydrochloride is used, the concentration thereof is preferably 5 M or more.

The lysis solution is not particularly limited as long as it contains such a chaotropic substance, however, it may contain a surfactant for the purpose of disrupting a cell membrane or denaturing a protein contained in cells. The surfactant is not particularly limited as long as it is a surfactant to be generally used for extracting nucleic acids from cells or the like, but examples thereof include nonionic surfactants such as Triton-based surfactants (such as Triton-X) and Tween-based surfactants (such as Tween 20); and anionic surfactants such as sodium n-lauroyl sarcosine (SDS). However, it is particularly preferred to use a nonionic surfactant in an amount in the range of 0.1 to 2%. Further, it is preferred that the lysis solution contains a reducing agent such as 2-mercaptoethanol or dithiothreitol. The lysis solution may be a buffer, but preferably has a neutral pH in the range of 6 to 8. In view of this, specifically, it is preferred that the lysis solution contains 4 to 7 M of a guanidine salt, 0 to 5% of a nonionic surfactant, 0 to 0.2 M of a reducing agent, and the like.

The nucleic acid-binding solid-phase carrier is not particularly limited as long as it is a solid having a hydrophilic surface capable of adsorbing nucleic acids, in other words, retaining nucleic acids through a reversible physical bond in the presence of a chaotropic ion. Specifically, a substance containing silicon dioxide, for example, silica, glass, diatomaceous earth, or a substance obtained by subjecting such a substance to a surface treatment by chemical modification is preferred, and a complex thereof with a magnetic material, a superparamagnetic metal oxide, or the like is more preferred. In the case where a surface treatment by chemical modification is performed, the substance may be moderately charged with positive electricity to such an extent that it does not inhibit the reversible bond thereof to nucleic acids.

Examples of the form of the nucleic acid-binding solid-phase carrier include a particle, a filter, a bag, a dish, and a reaction container, but it is not particularly limited. Among these, the particle form is more preferred in view of efficiency of adsorption and elution. In this case, the particle diameter is not particularly limited, but may be from 0.05 to 500 μm, and is preferably from 1 to 100 μm, and particularly preferably from 1 to 10 μm.

The washing solution preferably contains substantially no organic solvents such as ethanol and isopropyl alcohol and chaotropic substances. This washing solution is preferably water or a low salt concentration aqueous solution, and in the case of a low salt concentration aqueous solution, the low salt concentration aqueous solution is preferably a buffer. The salt concentration of the low salt concentration aqueous solution is preferably 100 mM or less, more preferably 50 mM or less, and most preferably 15 mM or less. The lower limit of the salt concentration of the low salt concentration aqueous solution is not particularly limited, but is preferably 0.1 mM or more, more preferably 1 mM or more, and most preferably 10 mM or more. This solution may contain a surfactant such as Triton, Tween, or SDS, and the pH of the solution is not particularly limited. A salt for forming the buffer is not particularly limited, however, a salt such as Tris, HEPES, PIPES, or phosphate is preferably used.

When washing is performed more than once, the washing solutions having the same components may be used, but the washing solutions having different components may be used. For example, as the washing solution to be used immediately after the lysis treatment, a solution containing a guanidine salt may be used, however, it is particularly preferred that this washing solution contains 4 to 7 M of a guanidine salt and 0 to 5% of a nonionic surfactant.

Also, the reverse transcription reaction mixture is not particularly limited as long as it contains a reverse transcriptase, dNTP, and a primer (an oligonucleotide) for the reverse transcriptase. It is preferred that the reverse transcription reaction mixture contains BSA (bovine serum albumin) or gelatin as a reaction inhibition inhibitor. The solvent is preferably water, and the reverse transcription reaction mixture preferably contains substantially no organic solvents such as ethanol and isopropyl alcohol and chaotropic substances. Further, the reverse transcription reaction mixture preferably contains an appropriate concentration of a salt so as to serve as a buffer for the reverse transcriptase. The salt for forming a buffer is not particularly limited as long as it does not inhibit the enzymatic reaction, however, a salt such as Tris, HEPES, PIPES, or phosphate is preferably used. The reverse transcriptase is not particularly limited, however, a reverse transcriptase derived from avian myeloblast virus, Ras associated virus type 2, mouse molony murine leukemia virus, or human immunodefficiency virus type 1, or the like can be used.

The eluent contains solutes such as an enzyme, a substrate, and a salt for successively treating the cDNA synthesized by reverse transcription. The eluent preferably contains BSA (bovine serum albumin) or gelatin as a reaction inhibition inhibitor. The solvent is preferably water, and the eluent is more preferably an eluent containing substantially no organic solvents such as ethanol and isopropyl alcohol and chaotropic substances.

For example, in the case where the cDNA is successively amplified by PCR after the reverse transcription reaction, the eluent is not particularly limited as long as it contains a DNA polymerase, dNTP, and primers (oligonucleotides) for the DNA polymerase. The eluent may further contain a TaqMan probe or a probe for real time PCR such as a molecular beacon probe or a cycling probe, or an intercalating fluorescent dye such as SYBR green. Further, it is preferred that the eluent contains an appropriate concentration of a salt so as to serve as a buffer for the DNA polymerase. The salt for forming a buffer is not particularly limited as long as it does not inhibit the enzymatic reaction, however, a salt such as Tris, HEPES, PIPES, or phosphate is preferably used. The DNA polymerase is not particularly limited, and there are an enormous number of commercially available products such as Taq polymerase, Tfi polymerase, Tth polymerase, and modified forms thereof.

The concentration of the dNTP or the salt to be contained in the reverse transcription reaction mixture or the eluent may be set so as to be suitable for the reaction using the dNTP and the salt, however, the concentration of the dNTP may be set to generally 10 to 1000 µM, preferably 100 to 500 µM, the concentration of $Mg^{2+}$ may be set to generally 1 to 100 mM, preferably 5 to 10 mM, and the concentration of $Cl^-$ may be set to generally 1 to 2000 mM, preferably 200 to 700 mM. The total ion concentration is not particularly limited, but may be set to 50 mM or more, preferably 100 mM or more, more preferably 120 mM or more, further more preferably 150 mM or more, still further more preferably 200 mM or more. The upper limit thereof is preferably 500 mM or less, more preferably 300 mM or less, further more preferably 200 mM or less. The concentration of each of the oligonucleotides for use as the primers is from 0.1 to 10 µM, preferably from 0.1 to 1 µM. If the concentration of BSA or gelatin is 1 mg/mL or less, the effect of inhibiting the reaction inhibition is low, and if it is 10 mg/mL or more, the reverse transcription reaction or the following enzymatic reaction may be inhibited, and therefore, the concentration of BSA or gelatin is preferably from 1 to 10 mg/mL. In the case of using gelatin, the origin of the gelatin may be exemplified by cattle skin, pig skin, and cattle bone, but is not particularly limited. If it is difficult to dissolve gelatin, it may be dissolved by heating.

cDNA Synthesis Method

Specifically, cDNA may be synthesized as follows.

Adsorption Step

First, an appropriate amount of the lysis solution is placed in a tube suitable for the purpose such as an Eppendorf microcentrifuge tube or a plastic tube, and a sample from which RNA is extracted and a nucleic acid-binding solid-phase carrier are mixed with the lysis solution. Then, the sample is homogenized by a homogenizer, a vortex mixer, or the like, and then, RNA is adsorbed on the carrier.

Washing Step

Subsequently, the lysis solution is removed from the tube. Thereafter, the reverse transcription reaction mixture may be directly added to the carrier having the RNA adsorbed thereon, however, it is preferred that the carrier having the RNA adsorbed thereon is washed with an appropriate amount of the washing solution for reducing the carryover of the solutes from the previous step and accurately adjusting the salt concentration by removing contaminants nonspecifically adsorbed on the carrier and replacing the solution. The number of washing operations is not particularly limited, however, washing may be performed once to several times. When the washing is performed more than once, it is preferred that a washing solution which contains a guanidine salt is used in the first wash, and a washing solution which does not contain a guanidine salt is used in the last wash. For example, as the washing solution which contains a guanidine salt, a washing solution containing 4 to 7 M of a guanidine salt and 0 to 5% of a nonionic surfactant can be used, and as the washing solution which does not contain a guanidine salt, a washing solution composed of water or a low salt concentration aqueous solution can be used.

In the cDNA synthesis method according to the invention, the "washing" refers to an operation in which a substance nonspecifically bound to the carrier other than RNA is removed from the carrier by bringing the carrier having the RNA bound thereto and the washing solution into contact with each other and then separating the carrier and the washing solution from each other again. The specific separation method varies depending on the form of the carrier to be used, however, in the case where the carrier is in the form of particles such as beads, centrifugation, filtration, column chromatography, or the like can be used.

Reverse Transcription Step

Subsequently, the washing solution is removed from the tube, and the reverse transcription reaction mixture is added to the carrier having the RNA adsorbed thereon to carry out a reverse transcription reaction, whereby cDNA is synthesized. The reverse transcription reaction mixture contains a reverse transcriptase, dNTP, and a primer for the reverse transcriptase, and therefore can be directly used for the reverse transcription reaction while keeping the RNA adsorbed on the carrier. In the reverse transcription reaction, the reverse transcription reaction mixture containing the carrier having the RNA adsorbed thereon may be used partially or entirely. In the case where the mixture is used partially, it is preferred to dilute the mixture with a buffer adjusted for the reverse transcriptase. As the buffer adjusted for the reverse transcriptase, a solution having the same components as those of the reverse transcription reaction mixture may be used, however, it is not particularly limited as long as the salt concentration is appropriately adjusted, and it does not matter whether the reverse transcriptase, dNTP, or the primer for the reverse transcriptase is added or not. In the method according to the invention, this reverse transcription step does not include a step of removing the carrier. In other words, by performing the reverse transcription reaction without releasing the RNA adsorbed on the carrier from the carrier, it is possible to synthesize cDNA which can be efficiently used in the following reaction. Therefore, for example, it is preferred to perform the reverse transcription reaction at a low temperature. The temperature in the reverse transcription reaction may be lower than 50° C., but is preferably lower than 45° C., more preferably lower than 40° C., further more preferably lower than 35° C. The lower limit of the temperature in the reverse transcription reaction is preferably 20° C. or higher, more preferably 25° C. or higher, further more preferably 30° C. or higher.

Washing Step

After the reverse transcription step, the reverse transcription reaction mixture is removed from the tube, and the eluent may be directly added to the carrier having the RNA adsorbed thereon, however, it is preferred that the carrier having the RNA adsorbed thereon is washed with an appropriate amount of the washing solution for reducing the carryover of the solutes from the previous step and accurately adjusting the salt concentration by removing contaminants nonspecifically adsorbed on the carrier and replacing the solution. The number of washing operations is not particularly limited, however, washing may be performed once to several times. As the washing solution, a washing solution composed of water or a low salt concentration aqueous solution is preferred.

Elution Step

After the washing, the washing solution is removed, and an appropriate amount of the eluent is added to the carrier. Then, these are mixed by a vortex mixer or the like, whereby cDNA bound to the carrier is released from the carrier. At this time, the eluent may be heated for accelerating the elution of the cDNA. The heating temperature is not particularly limited, but may be higher than 40° C., and is preferably 50° C. or higher, more preferably 60° C. or higher. The upper limit of the heating temperature is not particularly limited, but is preferably 70° C. or lower, more preferably 65° C. or lower, further more preferably 60° C. or lower, and most preferably 60° C. As for the heating method, the eluent which is preheated may be added, or after the eluent is added to the carrier, heating may be performed. The heating time is not particularly limited, but is preferably about 30 seconds to 10 minutes. After the elution, the carrier is removed, whereby the supernatant can be isolated. The thus synthesized cDNA can be efficiently used for a variety of applications such as a polymerase reaction including PCR.

In the case where the carrier and the supernatant are separated from each other in the washing step or the like, the separation can be performed by precipitating the carrier through centrifugation or the like. However, when the carrier contains a magnetic material, the separation can be easily performed using a magnet or the like.

Use of Synthesized cDNA

For example, by adding a buffer (×10 solution) for the DNA polymerase reaction or the like to the eluate in an amount one-tenth the amount of the eluate, a PCR reaction can be performed, however, it is preferred that the salt concentration of the eluent is previously optimized for the enzymatic reaction, and the eluent contains a DNA polymerase, dNTP, and primers for the DNA polymerase. In this case, the eluate can be directly used for the DNA polymerase reaction. At this time, in the DNA polymerase reaction, the reaction mixture may be used partially or entirely. In the case where the reaction mixture is used partially, it is preferred to dilute the mixture with a buffer adjusted for the DNA polymerase. As the buffer adjusted for the DNA polymerase, a solution having the same components as those of the eluent may be used, however, it is not particularly limited as long as the salt concentration is appropriately adjusted, and it does not matter whether the DNA polymerase, dNTP, or the primers for the DNA polymerase may be added or not.

The DNA polymerase reaction may be performed under the conditions suitable for the DNA polymerase to be used. After the DNA polymerase reaction, the amplified cDNA can be used for a variety of applications such as preparation of a library.

cDNA Synthesis Kit

The cDNA synthesis kit according to the invention includes (1) a neutral lysis solution containing 4 to 7 M of a guanidine salt, 0 to 5% of a nonionic surfactant, and 0 to 0.2 M of a reducing agent, (2) a nucleic acid-binding solid-phase carrier, (3) a first washing solution containing 4 to 7 M of a guanidine salt and 0 to 5% of a nonionic surfactant, (4) a second washing solution composed of water or a low salt concentration aqueous solution, (5) a reverse transcription reaction mixture containing a reverse transcriptase and dNTP, and (6) a DNA amplification mixture containing a DNA polymerase and dNTP. With the use of this kit, only by adding a primer for reverse transcription corresponding to the target gene to the reverse transcription reaction mixture, and only adding primers for DNA amplification to the DNA amplification mixture, the cDNA synthesis according to the invention and the cDNA amplification subsequent to the cDNA synthesis can be easily and efficiently performed.

Further, this kit may contain a primer for reverse transcription and/or primers for DNA amplification. According to this configuration, a cDNA synthesis kit for a specific gene can be provided.

The constituent components such as the lysis solution, the washing solution, and the eluent of this kit are in accordance with those described in the reagents for cDNA synthesis.

EXAMPLES

Experimental Method (1) Adsorption Step

To 150 µL of a serum sample (collected from a patient suffering from influenza A) placed in a 1.5-mL Eppendorf microcentrifuge tube, 350 µL of a lysis solution (containing 5.5 M guanidine thiocyanate, 2% Triton X-100, and 0.15 M 2-mercaptoethanol) was added and sufficiently mixed, whereby blood cells were lysed. To this mixture containing lysed cells, 20 µL of magnetic silica particles (NPK-401, manufactured by Toyobo Co., Ltd.) were added, and the mixture was stirred by a vortex mixer at room temperature for 5 minutes. Thereafter, this microcentrifuge tube was placed on a magnetic stand (MGS-101, Toyobo Co., Ltd.) to collect the magnetic silica particles, and the supernatant was removed.

(2) Washing Step

Subsequently, the microcentrifuge tube was removed from the magnetic stand, and 350 µL of a washing solution I (containing 7M guanidine hydrochloride) was added to the tube and sufficiently mixed. Thereafter, the tube was placed on the magnetic stand again to collect the magnetic silica particles, and the supernatant was removed, whereby the magnetic particles were washed. Subsequently, in the same manner, the particles were washed with 450 µL of a washing solution II (containing 5 mM Tris-HCl buffer), and the supernatant was removed at the end of the washing.

(3) Reverse Transcription Step

To the particles collected by removing the supernatant, 20 µL of a reverse transcription reaction mixture was added to suspend the particles. Then, the microcentrifuge tube was heated to 40° C. for 10 minutes by a tube heater to carry out the reverse transcription reaction. Thereafter, the microcentrifuge tube was placed on the magnetic stand to collect the magnetic silica particles, and the supernatant was removed.

(4) Washing Step

To this sample, 450 µL of the washing solution II was added, and the resulting mixture was stirred by a vortex mixer

(5) Example 1

Elution in Water and PCR Reaction

To the particles collected by removing the supernatant in (4), 20 µl of water was added to suspend the particles, and the resulting mixture was heated to 65° C. for minutes, and then stirred by a vortex mixer at room temperature for 5 seconds. Thereafter, this microcentrifuge tube was placed on the magnetic stand to collect the magnetic silica particles, and the supernatant was collected.

A 4-µL aliquot of the collected supernatant was added to 16 µL of a preparation solution for a PCR reaction, whereby a reaction mixture in a total amount of 20 µL was prepared. This reaction mixture was placed in a PCR apparatus (light cycler 480, manufactured by Roche, Ltd.), and a real time PCR reaction was performed. The luminance was measured at the end of each cycle.

(6) Example 2

Elution in PCR Reaction Mixture and PCR Reaction

To the particles collected by removing the supernatant in (4), 20 µL of a PCR reaction mixture was added to suspend the particles, and the resulting mixture was heated to 65° C. for 2 minutes, and then stirred by a vortex mixer at room temperature for 5 seconds. Thereafter, this microcentrifuge tube was placed on the magnetic stand, and the supernatant was collected.

The thus obtained 20 µL of the PCR reaction mixture was directly placed in the PCR apparatus, and a real time PCR reaction was performed. The luminance was measured at the end of each cycle.

(7) Example 3

Related Art Method

To the particles collected by removing the supernatant in (2), 20 µl of water was added to suspend the particles, and the resulting mixture was heated to 60° C. for minutes. Thereafter, this microcentrifuge tube was placed on the magnetic stand to collect the magnetic silica particles, and the supernatant was collected.

A 4-µL aliquot was taken out from the collected supernatant and added to 16 µl of a preparation solution for a reverse transcription reaction, whereby a reaction mixture in a total amount of 20 µl was prepared. Then, the microcentrifuge tube was heated to 40° C. for 10 minutes by a tube heater to carry out the reverse transcription reaction.

A 4-µL aliquot was taken out from the mixture after completion of the reaction and added to 16 µl of a preparation solution for a PCR reaction, whereby a reaction mixture in a total amount of 20 µl was prepared. This reaction mixture was placed in the PCR apparatus, and a real time PCR reaction was performed. The luminance was measured at the end of each cycle.

TABLE 1

| | Reagent | Addition amount (µL) | Concentration | Final concentration | Unit |
|---|---|---|---|---|---|
| Reverse transcription reaction mixture | AMV reverse transcriptase (Nippon Gene Co., Ltd.) | 0.2 | 20.0 | 0.2 | units/µL |
| | dNTP | 1.6 | 10.0 | 0.8 | mM |
| | Buffer* | 4.0 | | | |
| | Primer R** | 1.0 | 10.0 | 0.5 | µM |
| | BSA | 2.0 | 20.0 | 2.0 | mg/mL |
| | DW | 11.2 | | | |
| PCR reaction mixture | Gene Taq NT PCR enzyme (Nippon Gene Co., Ltd.) | 0.2 | 5.0 | 0.05 | units/µL |
| | dNTP | 1.0 | 10.0 | 0.5 | mM |
| | Buffer* | 4.0 | | | |
| | Primer F** | 1.0 | 10.0 | 0.5 | µM |
| | Primer R** | 1.0 | 10.0 | 0.5 | µM |
| | Probe (TaqMan)** | 0.4 | 12.5 | 0.25 | µM |
| | BSA | 2.0 | 20.0 | 2.0 | mg/mL |
| | DW | 10.4 | | | |
| Preparation solution for reverse transcription reaction | AMV reverse transcriptase (Nippon Gene Co., Ltd.) | 0.2 | 20.0 | 0.2 | units/µL |
| | dNTP | 1.6 | 10.0 | 0.8 | mM |
| | Buffer* | 4.0 | | | |
| | Primer R** | 1.0 | 10.0 | 0.5 | µM |
| | BSA | 2.0 | 20.0 | 2.0 | mg/mL |
| | DW | 7.2 | | | |

TABLE 1-continued

| Reagent | | Addition amount (μL) | Concentration | Final concentration | Unit |
|---|---|---|---|---|---|
| Preparation solution for PCR reaction | Gene Taq NT PCR enzyme (Nippon Gene Co., Ltd.) | 0.2 | 5.0 | 0.05 | units/μL |
| | dNTP | 1.0 | 10.0 | 0.5 | mM |
| | Buffer* | 4.0 | | | |
| | Primer F** | 1.0 | 10.0 | 0.5 | μM |
| | Primer R** | 1.0 | 10.0 | 0.5 | μM |
| | Probe (TaqMan)** | 0.4 | 12.5 | 0.25 | μM |
| | BSA | 2.0 | 20.0 | 2.0 | mg/mL |
| | DW | | | | |

*Composition of the buffer (35 mM MgCl$_2$, 125 mM Tris (pH 9.0), 250 mM KCl)
**Base sequences of the primers and the probe
Primer F: GAC CAA TCC TGT CAC CTC TGA C (SEQ ID NO: 1)
Primer R: AGG GCA TTT TGG ACA AAG CGT CTA (SEQ ID NO: 2)
TaqMan probe: FAM-TGC AGT CCT CGC TCA CTG GGC ACG-TAMRA (SEQ ID NO: 3)

(8) Example 4

Case where Washing Step after Reverse Transcription Step was Omitted

In the same manner as in Examples 1 and 2 described above except that the washing step (4) after the reverse transcription step was omitted, cDNA was synthesized and PCR was performed.

Results

The results obtained by performing the real time PCR reaction under the same conditions in Examples 1 to 3 are shown in FIG. 1.

The number of cycles (Ct value) at the takeoff point of the amplification curve obtained in Example 1 (reverse transcription reaction→washing→elution in water) was smaller by about 2 cycles than the Ct value obtained in Example 3 (the related art method). Further, the Ct value obtained in Example 2 (reverse transcription reaction→washing→elution in PCR reaction mixture) was smaller by about 2 than the Ct value obtained in Example 1, and smaller by about 4 than the Ct value obtained in Example 3.

Figure 2:
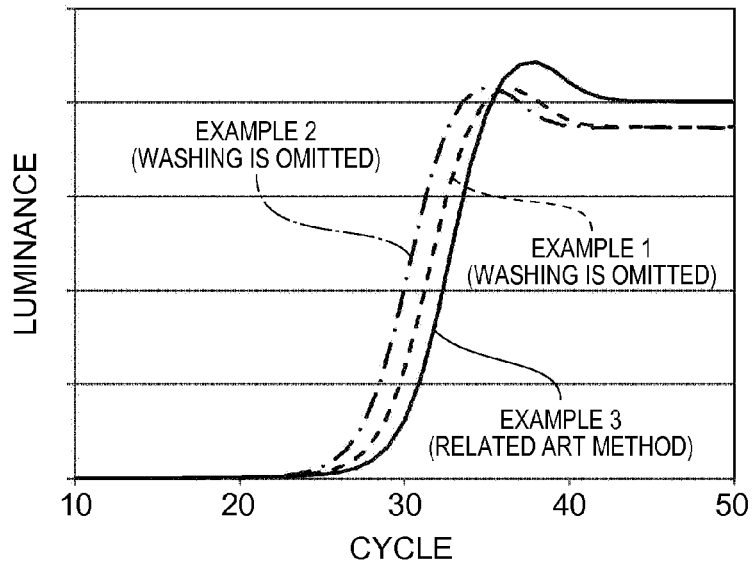
FIG. 2 is a graph showing the results obtained by performing a PCR reaction without performing a washing step after performing a reverse transcription reaction on a carrier in an example of the invention.

Next, the results obtained by treating the samples without performing the washing step (4) in (8) are shown in FIG. 2.

Although a higher detection sensitivity than in the related art method was obtained, the Ct value was increased than in the case of performing the washing (FIG. 1). This is considered to be because by omitting the washing, the residual reverse transcription reaction mixture which was not removed by removing the supernatant inhibited the PCR reaction.

Outline

In this manner, the highest PCR detection sensitivity was obtained in Example 2, and therefore, the method of Example 2 is an effective method because it enables detection with higher sensitivity than the related art method. The second highest detection sensitivity was obtained in Example 1, and the method of Example 1 enables detection with higher sensitivity than the related art method although the method of Example 1 is inferior to the method of Example 2.

Further, in Examples 1 and 3, the entire amount of the obtained cDNA was dissolved in water once, and therefore, the obtained entire amount cannot be used in the reaction. However, in Example 2, the obtained cDNA can be directly eluted in the PCR reaction mixture, and therefore, the amount of the PCR reaction mixture can be decreased to a very small amount, and thus, the reaction can be made more efficient. Further, in Examples 1 and 2, the extraction can be performed in the form of cDNA reverse-transcribed from the RNA, and therefore, long-term storage can be achieved stably as compared with the case of Example 3 (related art method) in which storage has to be performed in the form of RNA. Further, since DNA is more stable than RNA and can be stored at a higher temperature than RNA (RNA: −80° C., DNA: −20° C.), the storage cost is decreased as compared with the case of the related art.

The entire disclosure of Japanese Patent Application No. 2013-050659, filed Mar. 13, 2013 is expressly incorporated by reference herein.

What is claimed is:

1. A cDNA synthesis method, comprising:
   mixing a lysis solution containing a chaotropic substance and a nucleic acid-binding solid-phase carrier in a sample containing a ribonucleic acid (RNA), thereby adsorbing the RNA on the carrier;
   reverse-transcribing the RNA adsorbed on the carrier while keeping the RNA adsorbed on the carrier in a reverse transcription reaction mixture, thereby synthesizing cDNA; and
   eluting the synthesized cDNA by adding an eluent that contains a DNA-dependent DNA polymerase, dNTP, and primers for DNA amplification,
   wherein the cDNA is not amplified by polymerase chain reaction (PCR) prior to eluting.

2. The cDNA synthesis method according to claim 1, further comprising washing the carrier having the RNA adsorbed thereon with a washing solution before the reverse transcription.

3. The cDNA synthesis method according to claim 1, further comprising washing the carrier having the RNA adsorbed thereon with a washing solution which does not contain an organic solvent after the reverse transcription.

4. The cDNA synthesis method according to claim 1, wherein the reverse transcription reaction mixture contains a reverse transcriptase, dNTP, and a primer for reverse transcription.

5. The cDNA synthesis method according to claim 1, wherein the reverse transcription reaction mixture and/or the eluent contains BSA.

6. The cDNA synthesis method according to claim 1, wherein in the reverse transcription, the RNA is reverse-transcribed at a temperature lower than 50° C.

7. The cDNA synthesis method according to claim 1, wherein the carrier is a magnetic particle.

* * * * *